United States Patent
Bock et al.

(10) Patent No.: US 9,393,181 B2
(45) Date of Patent: Jul. 19, 2016

(54) DENTAL MATERIALS WITH IMPROVED HYDROLYSIS STABILITY BASED ON PHTHALIC ACID MONOMERS

(71) Applicants: Thorsten Bock, Tosters (AT); Urs Karl Fischer, Arbon (CH); Iris Lamparth, Grabs (CH); Norbert Moszner, Mauren (LI); Volker Rheinberger, Vaduz (LI)

(72) Inventors: Thorsten Bock, Tosters (AT); Urs Karl Fischer, Arbon (CH); Iris Lamparth, Grabs (CH); Norbert Moszner, Mauren (LI); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 52 days.

(21) Appl. No.: 13/630,491

(22) Filed: Sep. 28, 2012

(65) Prior Publication Data
US 2013/0090404 A1  Apr. 11, 2013

(30) Foreign Application Priority Data
Oct. 6, 2011 (EP) .................................... 11184237

(51) Int. Cl.
| A61K 6/00 | (2006.01) |
| A61K 6/083 | (2006.01) |
| C08F 2/50 | (2006.01) |

(52) U.S. Cl.
CPC .............. *A61K 6/0023* (2013.01); *A61K 6/083* (2013.01)

(58) Field of Classification Search
CPC ......... A61K 6/0023; A61K 6/083; C08F 2/50
USPC ....................................... 522/28, 71, 77, 116
See application file for complete search history.

(56) References Cited

U.S. PATENT DOCUMENTS

| 4,521,550 A | 6/1985 | Bowen |
| 7,582,686 B2 | 9/2009 | Hoffmann et al. |
| 2004/0266906 A1 | 12/2004 | Klee et al. |

FOREIGN PATENT DOCUMENTS

| JP | 57105409 | 6/1982 | |
| JP | 02-130555 | * 5/1990 | ............... G03G 5/05 |
| JP | 5097621 | 4/1993 | |
| JP | 2011057567 | 3/2011 | |

OTHER PUBLICATIONS

Ikemura et al., machine English tranlsation of JP 2011-057657.*
Miki et al., English translation of JP 02-251507 (pub Oct. 9, 1990).*
Database WPI, Week 201127, Thomson Scientific, London, GB, AN 2011-D06252 (corresponding to JP 2011 057567), (2011).
Database WPI, Week 198232, Thomson Scientific, London, GB, AN 1982-66602E (corresponding to JP 57 105409), (1982).
Database WPI, Week 199320, Thomson Scientific, London, GB, AN 1993-164315 (corresponding to JP 5 097621), (1993).
Chang et al., "4-META use in dentisry: A literature review", The journal of Prosthetic Dentistry, 2002, 216-224, vol. 84, No. 2.
Fujisawa et al., "1H-NMR Studies of the Interaction of Dental Adhesive Monomer, 4-META with Calcium", Dental Materials Journal, 1999, 54-62, vol. 18(1).

* cited by examiner

*Primary Examiner* — Michael Pepitone
*Assistant Examiner* — Jessica Roswell
(74) *Attorney, Agent, or Firm* — Ann M. Knab; Thad McMurray

(57) ABSTRACT

Dental material which contains a polymerizable phthalic acid derivative of the general Formula I:

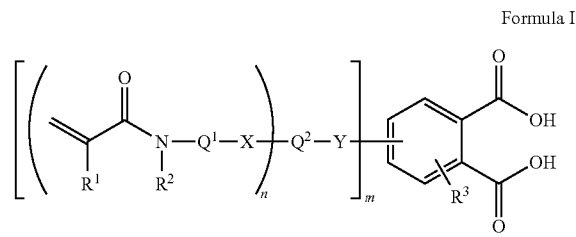

Formula I with $R^1$=H, methyl or a $C_1$-$C_5$ alkyl residue; $R^2$=H, a phenyl, benzyl or $C_1$-$C_8$ alkyl residue; $Q^1$=is absent or is a $C_1$-$C_{15}$ alkylene residue, wherein the carbon chain can be interrupted by O or S; $Q^2$=is absent or a (n+1)-valent aliphatic $C_1$-$C_{20}$ residue, wherein the carbon chain can be interrupted by O or S and wherein $Q^1$ and $Q^2$ cannot be absent simultaneously; X=is absent, is O, S or (—CO—$NR^4$—)—, wherein $R^4$ is H, $CH_3$ or $C_2H_5$; Y=is absent, is O, S or (—CO—$NR^5$—)—, wherein $R^5$ is H, $CH_3$ or $C_2H_5$; n, m=independently of one another in each case mean 1, 2 or 3; $R^3$=H, $CH_3$, $C_2H_5$, Cl, Br or $OCH_3$, and wherein the two carboxyl groups of the benzene ring can together form an anhydride group.

21 Claims, No Drawings

DENTAL MATERIALS WITH IMPROVED HYDROLYSIS STABILITY BASED ON PHTHALIC ACID MONOMERS

CROSS-REFERENCE TO RELATED APPLICATIONS

This application claims the benefit of European Application No. 11184237 filed on Oct. 6, 2011, which is hereby incorporated by reference in its entirety.

TECHNICAL FIELD

The present invention relates to polymerizable phthalic acid monomers with high hydrolysis stability and their use as monomer component in adhesive dental materials, in particular for the preparation of dental adhesives and cements.

BACKGROUND 4-methacryloyloxyethyl trimellitic acid (4-MET) and the corresponding anhydride (4-META) display excellent adhesion properties as adhesive monomers in dental adhesives, both on the tooth structure and also on metallic substrates, and have therefore found use in many dentine adhesion promoters of very different generations as well as in metal primers (Chang et al., "4-META use in dentistry: a literature review", J. Prosthet. Dent. 87 (2002) 216-224). 4-META is very quickly hydrolyzed to 4-MET in aqueous solutions and it is assumed that 4-MET is responsible for the adhesion properties (S. Fujisawa, S. Ito, Dent. Mat. J. 18 (1999) 54-62).

However, aqueous solutions of 4-MET are not storage-stable, as the methacrylate group is hydrolytically split off. It was found that in aqueous solution, after only eight weeks' storage at 42° C., a large part of the original compound used is hydrolytically decomposed. Thus the use of 4-META and 4-MET in self-etching enamel-dentine adhesives which contain water as co-solvent is very problematic.

EP 1 681 283 A1 and corresponding U.S. Pat. No. 7,582,686, which is hereby incorporated by reference, discloses ether compounds of organic acids and anhydrides such as 4-(2-ethoxycarbonyl-allyloxy)-phthalic acid which are hydrolysis-stable and are said to be suitable for the preparation of self-etching dental adhesives. The hydrolysis stability of these compounds is, however, likewise unsatisfactory.

WO 03/035013 A1 and corresponding US 20040266906, which is hereby incorporated by reference, discloses aqueous, single-component self-etching dental adhesives with a pH of at most 2 which contain a polymerizable N-substituted alkylacrylic or acrylamide monomer which has at least one phosphonic acid or sulphonic acid group. The monomers are to be hydrolysis-stable.

SUMMARY

The object of the invention is to provide adhesive dental materials based on phthalic acid derivatives which are very well polymerizable, display a high hydrolysis stability under acid conditions, dissolve in polar solvents, promote good substrate adhesion on tooth structure and which are physiologically harmless.

DETAILED DESCRIPTION

The object is achieved according to the invention by dental materials which contain at least one polymerizable phthalic acid derivative of the general Formula I:

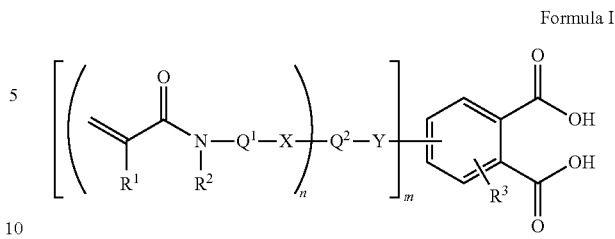

in which
$R^1$=H, methyl or a $C_1$-$C_5$ alkyl residue,
$R^2$=H, a phenyl, benzyl or $C_1$-$C_8$ alkyl residue,
$Q^1$=is absent or is a $C_1$-$C_{15}$ alkylene residue, wherein the carbon chain can be interrupted by O or S,
$Q^2$=is absent or is a (n+1)-valent aliphatic $C_1$-$C_{20}$ residue, wherein the carbon chain can be interrupted by O or S and wherein $Q^1$ and $Q^2$ cannot be dispensed with simultaneously,
X=is absent, is O, S or (—CO—$NR^4$—), wherein $R^4$ is H, $CH_3$ or $C_2H_5$, wherein X is absent if $Q^1$ is absent,
Y=is absent, is O, S or (—CO—$NR^5$—), wherein $R^5$ is H, $CH_3$ or $C_2H_5$, wherein Y is absent if $Q^2$ is absent,
n, m=independently of one another in each case mean 1, 2 or 3,
$R^3$=is H, $CH_3$, $C_2H_5$, Cl, Br or $OCH_3$, and
wherein the two carboxyl groups of the benzene ring can together form an anhydride group.

$Q^1$ preferably contains 0 to 4 and $Q^2$ preferably 0 to 6 heteroatoms. The phrase that the carbon chain is interrupted by O or S is to be understood to mean that the heteroatoms are integrated into the carbon chain, i.e. are bordered on both sides by carbon atoms. The number of carbon atoms is therefore at least 1 greater than the number of heteroatoms.

Compounds of the Formula I in which at least one of the variables has one of the following meanings are preferred:
$R^1$=H or methyl,
$R^2$=H or a $C_1$-$C_4$ alkyl residue,
$Q^1$=is absent or is a $C_2$-$C_{12}$ alkylene residue, wherein the carbon chain can be interrupted by O,
$Q^2$=is absent or is a (n+1)-valent aliphatic $C_1$-$C_{10}$ residue, wherein the carbon chain can be interrupted by O and wherein $Q^1$ and $Q^2$ cannot be absent simultaneously,
X=is absent, is O, S or (—CO—$NR^4$—), wherein $R^4$ is H, $CH_3$ or $C_2H_5$,
Y=is absent, is O or (—CO—$NR^5$—)—, wherein $R^5$ is $CH_3$ or $C_2H_5$,
n, m=independently of one another are 1 or 2,
$R^3$=H, $CH_3$, $C_2H_5$ or $OCH_3$.

Compounds in which all the variables have one of the preferred meanings are particularly preferred.

Compounds of the Formula I in which at least one of the variables and preferably all of the variables have one of the following meanings are quite particularly preferred:
$R^1$=H or methyl, in particular H,
$R^2$=H, methyl or ethyl, in particular methyl,
$Q^1$=a $C_1$-$C_{12}$ alkylene residue, in particular a $C_2$-$C_{12}$ alkylene residue, wherein the chain can be interrupted by O, preferably a linear $C_1$-$C_6$ alkylene residue;
$Q^2$=is absent or is a (n+1)-valent aliphatic $C_1$-$C_8$ residue, wherein the carbon chain can be interrupted by O and wherein $Q^1$ and $Q^2$ cannot be absent simultaneously,
X=is absent,
Y=is absent or is O, preferably O,
n, m=independently of one another are 1 or 2,
$R^3$=H, $CH_3$, or $OCH_3$.

Here too, compounds in which all the variables have one of the preferred meanings are particularly preferred.

It was found that the phthalic acid derivatives of the Formula (I) are characterized not only by a high resistance to hydrolysis and good dentine adhesion, but moreover also have a low cytotoxicity which is a considerable advantage for use in dental materials.

The polymerizable phthalic acid derivatives of the general Formula I can be easily prepared. For example, OH-functionalized phthalic acid derivatives can be reacted with Br-alkyl-functionalized (meth)acrylamides to form the phthalic acid derivatives of the general Formula I:

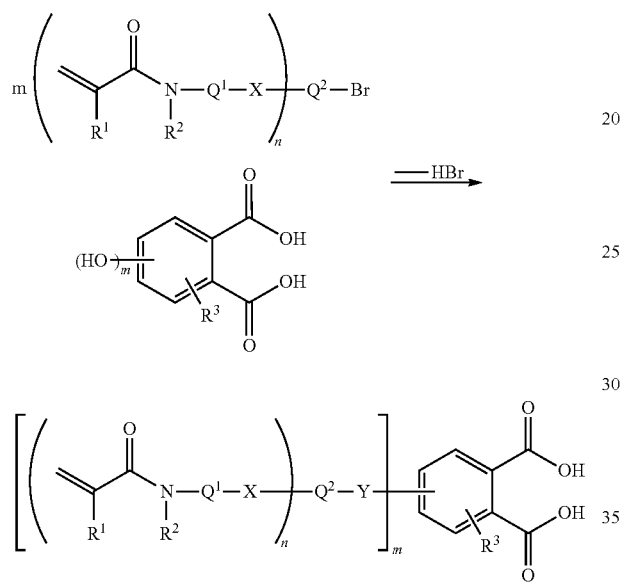

Specific example: Reaction of N-(11-bromoundecyl)-N-methyl acrylamide with 4-hydroxyphthalic Acid

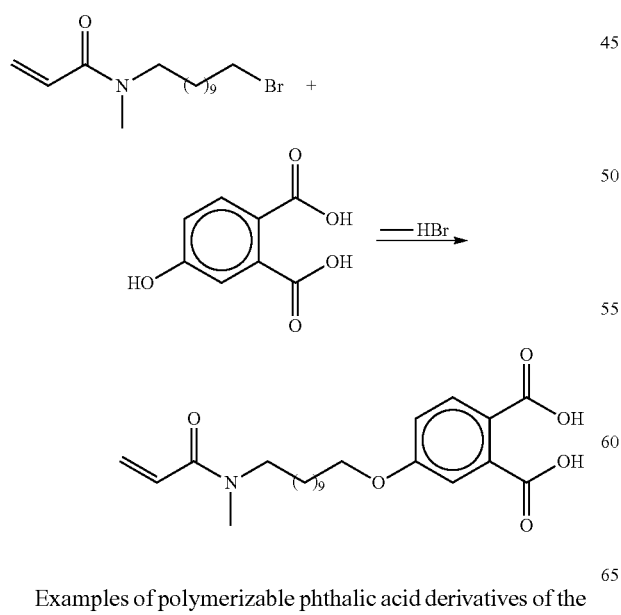

Examples of polymerizable phthalic acid derivatives of the general formula I preferred according to the invention are:

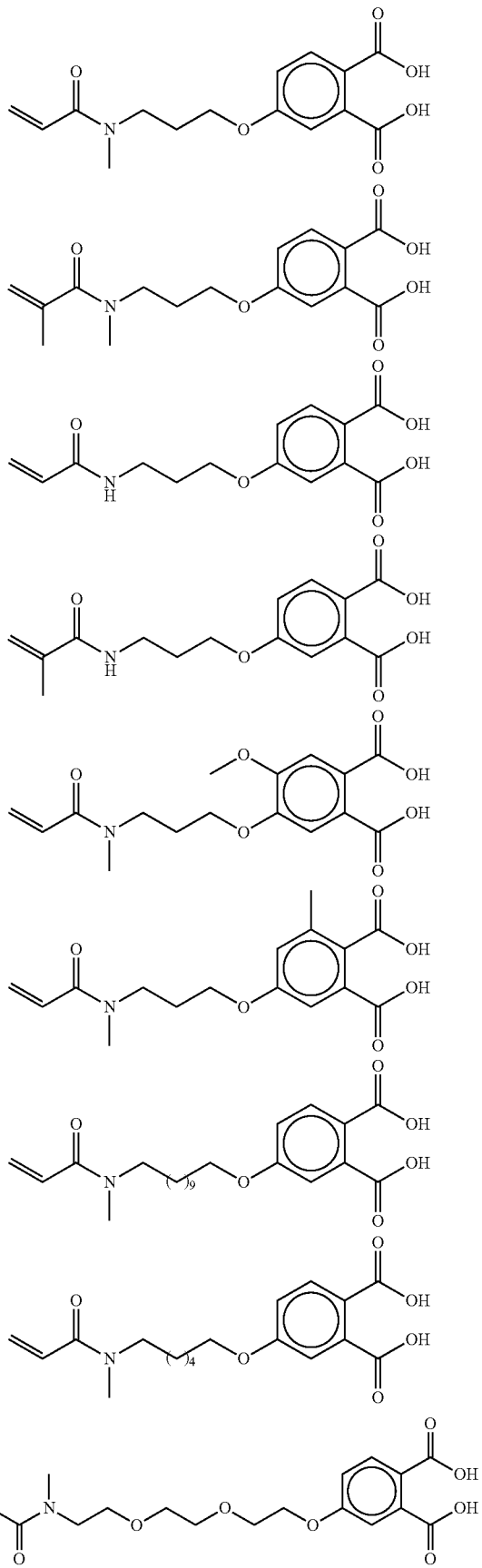

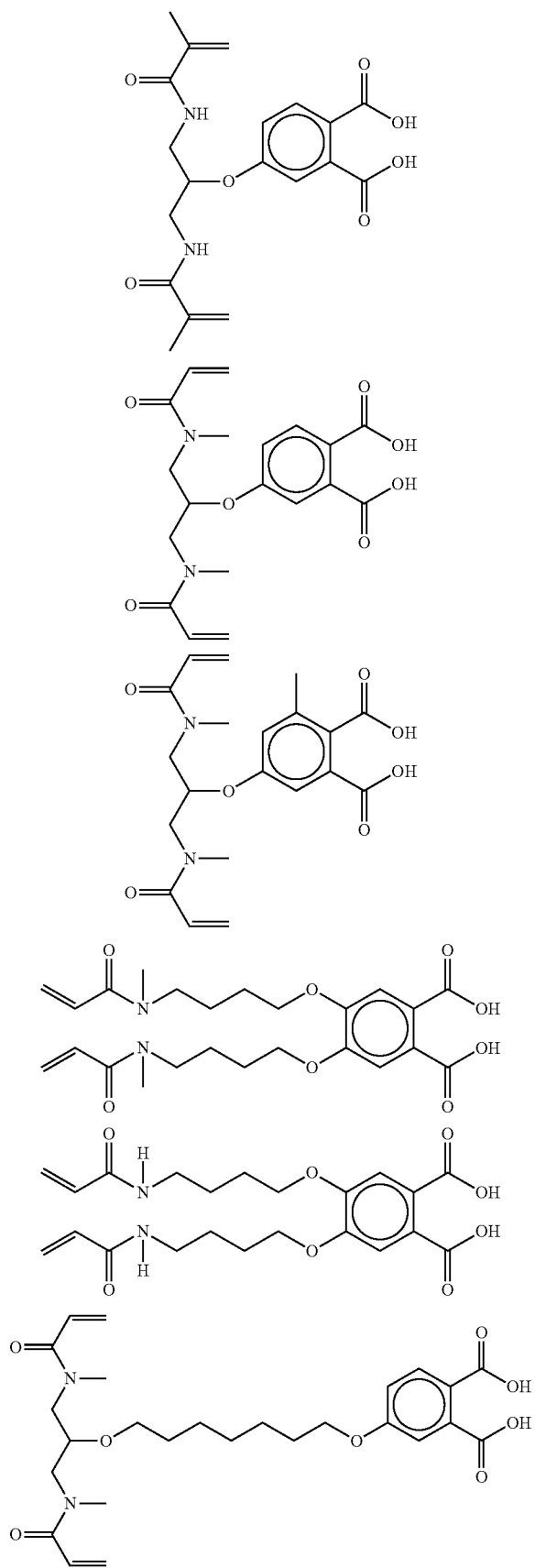
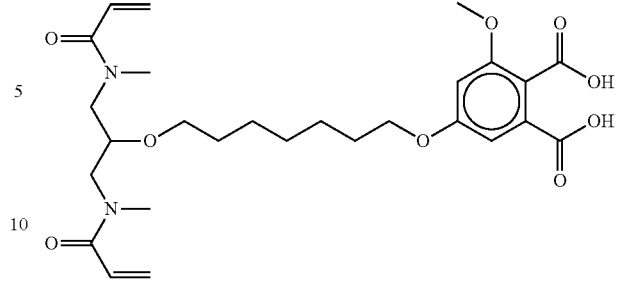

In addition to the polymerizable phthalic acid derivatives of the general Formula 1, the dental materials according to the invention preferably contain at least one additional radically polymerizable monomer (co-monomer), in particular at least one mono- or polyfunctional (meth)acrylic acid derivative. By monofunctional (meth)acrylic acid derivatives are meant compounds with one, by polyfunctional (meth)acrylic acid derivatives compounds with two or more, preferably 2 to 4 (meth)acrylic acid groups. Polyfunctional monomers have a cross-linking effect.

Mono- or polyfunctional (meth)acrylic acid derivatives preferred according to the invention are methyl, ethyl, hydroxyethyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), UDMA (an addition product of 2-hydroxyethyl methacrylate (HEMA) and 2,2,4-trimethylhexamethylene diisocyanate), di-, tri- or tetraethylene glycol di(meth)acrylate, trimethylolpropane tri(meth)acrylate, pentaerythritol tetra(meth)acrylate as well as glycerol di(meth)acrylate, 1,4-butanediol di(meth)acrylate, 1,10-decanediol di(meth)acrylate and 1,12-dodecanediol di(meth)acrylate.

Particularly preferred mono- or polyfunctional (meth)acrylic acid derivatives are N-mono- or disubstituted acrylamides, such as e.g. N-ethylacrylamide, N,N-dimethacrylamide, N-(2-hydroxyethyl)acrylamide or N-methyl-N-(2-hydroxyethyl)acrylamide, N-monosubstituted methacrylamides such as e.g. N-ethylmethacrylamide or N-(2-hydroxyethyl)methacrylamide as well as N-vinylpyrrolidone or allyl ethers. These monomers are characterized by a high hydrolysis stability and are particularly suitable as diluting monomers because of their relatively low viscosity.

Preferred polyfunctional (meth)acrylic acid derivatives with high hydrolysis stability are cross-linking pyrrolidones, such as e.g. 1,6-bis(3-vinyl-2-pyrrolidonyl)-hexane, or bisacrylamides such as methylene or ethylene bisacrylamide, bis(meth)acrylamides, such as N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by conversion from the corresponding diamines with (meth)acrylic acid chloride.

Mixtures of the above-named monomers are preferably used.

In addition to compounds of the Formula I and optionally the above-named co-monomers, the dental materials according to the invention can preferably also contain radically polymerizable, acid-group-containing monomers (adhesive monomers). Preferred acid groups are carboxylic acid groups, phosphonic acid groups, phosphoric acid groups and sulphonic acid groups.

Preferred monomers with polymerizable carboxylic acids are maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine and 4-vinylbenzoic acid.

Preferred phosphonic acid monomers are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid or 2-[4-(dihydroxyphosphoryl)-2-oxa-butyl]-acrylic acid ethyl- or -2,4,6-trimethylphenyl esters.

Preferred acidic polymerizable phosphoric acid esters are 2-methacryloyloxypropyl mono- or dihydrogen phosphate, 2-methacryloyloxyethylphenyl hydrogen phosphate, dipentaerythritol-pentamethacryloyloxyphosphate, 10-methacryloyloxydecyl dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propane-2-yl-dihydrogen phosphate.

Preferred polymerizable sulphonic acids are vinylsulphonic acid, 4-vinylphenylsulphonic acid or 3-(methacrylamido)propyl sulphonic acid.

Moreover, the dental materials according to the invention preferably also contain an initiator for radical polymerization.

Preferably, benzophenone, benzoin and derivatives thereof or α-diketones or derivatives thereof, such as 9,10-phenanthrenequinone, 1-phenyl-propane-1,2-dione, diacetyl or 4,4'-dichlorobenzil are used to initiate radical photopolymerization. Camphorquinone and 2,2-dimethoxy-2-phenyl-acetophenone are preferably used, and quite particularly preferably α-diketones combined with amines as reductants, such as e.g. 4-(dimethylamino)-benzoate, N,N-dimethylaminoethyl methacrylate, N,N-dimethyl-sym.-xylidine or triethanolamine. Norrish type I photoinitiators, above all acyl- or bisacylphosphine oxides, monoacyltrialkyl- or diacyldialkylgermanium compounds, such as e.g. benzoyltrimethylgermanium, dibenzoyldiethylgermanium or bis(4-methoxybenzoyl)diethylgermanium are also particularly preferred. Mixtures of the different photoinitiators can also be used, such as e.g. dibenzoyldiethylgermanium combined with camphorquinone and 4-dimethylaminobenzoic acid ethyl ester.

Preferably, redox-initiator combinations, such as e.g. combinations of benzoyl peroxide with N,N-dimethyl-sym.-xylidine or N,N-dimethyl-p-toluidine, are used as initiators for a polymerization carried out at room temperature. In addition, redox systems consisting of peroxides and reductants, such as e.g. ascorbic acid, barbiturates or sulphinic acids, are also particularly suitable.

The compositions used according to the invention furthermore preferably also contain organic or inorganic filler particles to improve the mechanical properties or to adjust the viscosity. Preferred inorganic particulate fillers are amorphous spherical materials based on oxides, such as $ZrO_2$ and $TiO_2$ or mixed oxides of $SiO_2$, $ZrO_2$ and/or $TiO_2$ with an average particle size of from 0.005 to 2.0 µm, preferably of from 0.1 to 1 µm, nanoparticulate or microfine fillers such as pyrogenic silicic acid or precipitation silicic acid with an average particle size of from 5 to 200 nm, preferably 10-100 nm, as well as minifillers such as quartz, glass ceramic or glass powder with an average particle size of from 0.01 to 1 µm, as well as X-ray-opaque fillers such as ytterbium trifluoride or nanoparticulate tantalum(V) oxide or barium sulphate with an average particle size of from 10 nm to 1000 nm, preferably 10-300 nm. The particle size is determined by electron microscopy (TEM and REM) or by scattered-light methods. Moreover, the compositions used according to the invention can contain further additives, above all solvents such as water or ethanol or corresponding solvent mixtures as well as e.g. stabilizers, flavourings, dyes, microbiocidal active ingredients, fluoride-ion-releasing additives, optical brighteners, plasticizers or UV absorbers.

Dental materials based on polymerizable phthalic acid derivatives of the general Formula I which contain the following constituents are particularly preferred:

a) 0.1 to 50 wt.-%, preferably 1 to 40 wt.-% and particularly preferably 2 to 30 wt.-% polymerizable phthalic acid derivative of the general Formula I,
b) 0.01 to 10 wt.-%, particularly preferably 0.1 to 3.0 wt.-% initiator,
c) 0 to 80 wt.-%, preferably 0 to 60 wt.-% and particularly preferably 5 to 50 wt.-% co-monomer,
d) 0 to 30 wt.-%, preferably 0 to 15 wt.-% adhesive monomer,
e) 0 to 80 wt.-% filler,
f) 0 to 70 wt.-%, preferably 0 to 60 wt.-% and particularly preferably 0 to 50 wt.-% solvent.

As co-monomer (c) the compositions preferably contain a polyfunctional monomer, i.e. a monomer with more than one radically polymerizable group, or a monomer mixture which contains predominantly polyfunctional monomers.

Furthermore compositions which contain water as solvent (f) are preferred. The solubility of the phthalic acid derivatives of the Formula (I) in polar solvents is good.

The preferred filler content depends on the desired use. Adhesives preferably contain 0 to 20 wt.-% and cements and composites preferably 20 to 80 wt.-% filler.

This also applies to the solvent content. Adhesives preferably contain 0 to 60 wt.-%, particularly preferably 5 to 60 wt.-% solvent. Adhesives which contain between 0 and 30 wt.-% and in particular between 2 and 20 wt.-% water are particularly preferred.

A subject of the invention is also the use of compounds of the Formula I for the preparation of dental materials, in particular adhesives or cements, quite particularly self-etching adhesives or cements.

The invention is explained in more detail below by the following non-limiting examples.

EXAMPLES

Example 1

Synthesis of 4-[11-(acryloyl-methyl-amino)-undecyloxy]phthalic acid (AAUPA)

$1^{st}$ Stage: 4-hydroxyphthalic Acid

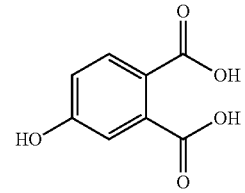 [SMILES: O=C(O)c1ccc(O)cc1C(=O)O]

Sodium hydroxide (251.9 g, 6.30 mol) was added in portions to 4-sulphophthalic acid (50% in water, 258.4 g, 0.525 mol) in a steel vessel accompanied by stirring. After the addition of approx. one third NaOH the increasingly more viscous mixture was heated to 180° C. Once the addition had ended the mixture was stirred for a further 2 h at 200° C. During cooling, the residue was dissolved in water (1000 ml). Conc. hydrochloric acid (620 ml, pH=1) was added accompanied by ice cooling. The solution was extracted with ethyl acetate (5×400 ml). The combined organic phases were dried over $Na_2SO_4$, filtered and concentrated on the rotary evaporator. The slightly yellow solid was recrystallized from ethyl acetate. 68.64 g (0.377 mol; 72% yield) of a white solid was obtained.

$^1$H-NMR (DMSO-d$_6$, 400 MHz): δ=6.90-6.93 (m, 2H), 7.69 (dd, 1H; J=2.4 Hz, 6.6 Hz), 10.41 (br s, 1H), 12.87 (br s, 2H).

$^{13}$C-NMR (DMSO-d$_6$, 100 MHz): δ=114.2, 116.2, 120.7, 131.5, 137.3, 160.1, 167.4, 169.5.

2$^{nd}$ Stage: 4-hydroxyphthalic anhydride

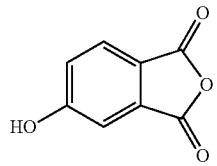

4-hydroxyphthalic acid (23.80 g, 0.131 mol) was heated for 1 h in an oil bath preheated to 200° C. After cooling the brownish solid was recrystallized from ethyl acetate/n-hexane (1:1). 15.82 g (96.4 mmol; 74% yield) of a white solid was obtained.

$^1$H-NMR (DMSO-d$_6$, 400 MHz): δ=7.25 (d, 1H; J=2.0 Hz), 7.28 (dd, 1H; J=2.0 Hz, 8.5 Hz), 7.89 (d, 2H, J=8.0 Hz), 11.44 (br s, 1H).

$^{13}$C-NMR (DMSO-d$_6$, 100 MHz): δ=111.0, 120.7, 123.0, 127.6, 133.9, 162.7, 163.2, 164.8.

3$^{rd}$ Stage: 11-methylamino-undecanol

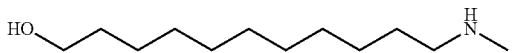

A solution of 11-bromoundecanol (25.12 g, 0.10 mol) and methylamine (41% in water, 127 ml, 1.50 mol) in ethanol (50 ml) was heated for 7 h to 70° C. and stirred for a further 16 h at ambient temperature. The solvent was distilled off. After cooling the white solid was dissolved in caustic soda (2N, 200 ml) and diethyl ether (300 ml). The phases were separated and the aqueous phase was extracted with diethyl ether (2×100 ml). The combined organic phases were dried over Na$_2$SO$_4$, filtered and concentrated on the rotary evaporator. The crude product was recrystallized from diethyl ether. 13.23 g (65.7 mmol, 67% yield) of a while solid (melting point: 58° C.) was obtained.

$^1$H-NMR (CDCl$_3$, 400 MHz): δ=1.24-1.38 (m, 14H), 1.43-1.58 (m, 4H), 2.41 (s, 3H), 2.55 (t, 2H; J=7.4 Hz), 3.57 (t, 2H; J=6.4 Hz).

$^{13}$C-NMR (CDCl$_3$, 100 MHz): δ=25.9, 27.3, 29.5, 29.6, 29.6, 29.6, 29.6, 29.8, 33.0, 36.4, 52.1, 62.4.

4$^{th}$ Stage: N-(11-hydroxy-undecyl)-N-methyl acrylamide

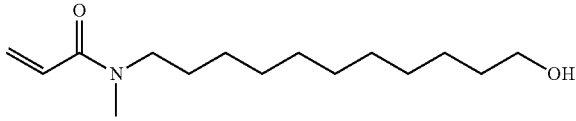 [SMILES: C=CC(=O)N(C)CCCCCCCCCCCO]

11-methylamino undecan-1-ol (10.07 g, 50.0 mmol) was dissolved in dichloromethane (30 ml). A solution of sodium hydroxide (2.40 g, 60.0 mmol) in water (30 ml) was added. The mixture was cooled to −5° C. and a solution of acrylic acid chloride (4.75 g, 52.5 mmol) and BHT (10 mg) in dichloromethane (30 ml) was added dropwise. Once the addition had ended the reaction mixture was stirred for 2 h at −5° C. and for a further 16 h at RT. Organic and aqueous phases were separated. The aqueous phase was saturated with NaCl and extracted with dichloromethane (2×50 ml). The combined organic phases were dried over Na$_2$SO$_4$, filtered and concentrated on the rotary evaporator. The crude product was purified by means of column chromatography (SiO$_2$/ethyl acetate). 10.38 g (40.6 mmol; 81% yield) of a yellowish liquid was obtained.

$^1$H-NMR (CDCl$_3$, 400 MHz): δ (2 isomers)=1.18-1.40 (m, 14H), 1.50-1.62 (m, 4H), 2.99 (s, 1.7H), 3.06 (s, 1.3H), 3.15 (br s, 1H), 3.34 (t, 1.2H; J=7.6 Hz), 3.41 (t, 0.8H; J=7.6 Hz), 3.59 (t, 2H; J=6.7 Hz), 5.66 (dd, 1H; J=2.0 Hz, 10.6 Hz), 6.29 (dq, 1H; J=2.0 Hz, 8.2 Hz), 6.57 (qd, 1H, J=4.4 Hz, 10.4 Hz).

$^{13}$C-NMR (CDCl$_3$, 100 MHz): δ=25.8, 26.6, 26.8, 27.1, 28.9, 29.3, 29.4, 29.4, 29.5, 32.7, 34.0, 35.4, 48.1, 50.1, 62.5, 127.6, 127.9, 166.2, 166.5.

5$^{th}$ Stage: N-(11-bromoundecyl)-N-methyl acrylamide

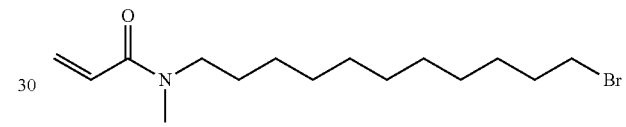

Diethylether (250 ml) was added to N-(11-hydroxy-undecyl)-N-methyl acrylamide (38.31 g, 0.150 mol) and BHT (10 mg). Phosphorus tribromide (13.53 g, 50.0 mmol) was added dropwise. The initially undissolved solid dissolved completely and a yellowish oil precipitated. The reaction mixture was stirred at ambient temperature. After 24 h water (100 ml) and dichloromethane (200 ml) were added and the phases were separated. The aqueous phase was extracted with dichloromethane (2×100 ml). The combined organic phases were dried over Na$_2$SO$_4$, filtered, concentrated on the rotary evaporator and dried on the fine vacuum. The yellowish oil was dissolved in dichloromethane (100 ml) and filtered via a fritted-glass filter filled with diatomaceous earth (n-hexane/ethyl acetate 1:1). The eluent was concentrated on the rotary evaporator and dried under a fine vacuum. 25.25 g (79.3 mmol; 53% yield) of a yellowish oil was obtained.

$^1$H-NMR (DMSO-d$_6$, 400 MHz): δ (2 isomers)=1.18-1.56 (m, 16H), 1.74-1.83 (m, 2H), 2.86 (s, 1.7H), 3.01 (s, 1.3H), 3.29-3.37 (m, 2H), 3.51 4.04 (t, 2H; J=6.8 Hz), 5.61-5.65 (m, 1H), 6.07-6.13 (m, 1H), 6.72 (dd, 1H; J=10.0 Hz, 16.2 Hz).

$^{13}$C-NMR (DMSO-d$_6$, 100 MHz): δ=25.9, 26.3, 26.6, 27.5, 28.1, 28.5, 28.7, 28.8, 28.8, 28.9, 32.2, 33.3, 34.8, 35.0, 46.9, 48.9, 126.6, 128,3, 128.7, 164.9, 165.0.

6$^{th}$ Stage: 4-[11-(acryloyl-methyl-amino)-undecyloxy]phthalic Acid (AAUPA)

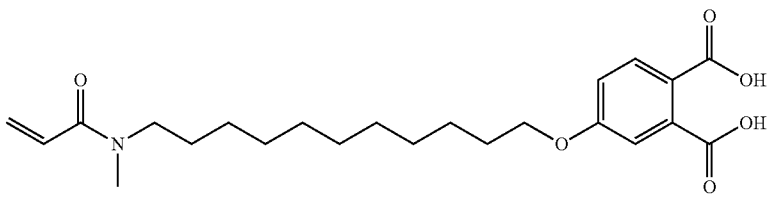 [SMILES: C=CC(=O)N(C)CCCCCCCCCCCOc1ccc(C(=O)O)c(C(=O)O)c1]

4-hydroxyphthalic anhydride (6.70 g; 40.8 mmol), BHT (10 mg) and N-(11-bromoundecyl)-N-methyl acrylamide (13.00 g; 40.8 mmol) were dissolved in N,N-dimethylformamide (100 ml). Potassium carbonate (5.64 g; 40.8 mmol) was added. The yellow suspension was stirred at RT. Water (200 ml) was added to the reaction mixture after 20 d and the whole stirred for 1 h at RT. An oily white solid precipitated from the initially cloudy solution. The solvent was decanted off. The residue was dissolved in dilute aqueous $Na_2CO_3$ solution (5%; 100 ml). The milky/cloudy aqueous phase was washed with MtBE (5×100 ml). Diluted hydrochloric acid (2N, 100 ml) was added to the water phase (pH=1) and extraction with MtBE (8×100 ml) took place. The combined extracts were dried over $Na_2SO_4$, filtered and concentrated on the rotary evaporator. Chloroform (150 ml) was added to the residue and the whole stirred at RT. After 20 h the suspension was filtered. The filtration residue was washed with chloroform (50 ml) and discarded. The filtrate was concentrated on the rotary evaporator. The residue was dissolved in chloroform (50 ml). Acetonitrile (50 ml) was added. After 72 h storage at −18° C. the solvent was decanted off and the residue dried under a fine vacuum. 3.84 g (9.2 mmol; 22% yield) of a white solid was obtained (melting point: 95° C.), which dissolves very well e.g. in ethanol or acetone.

$^1$H-NMR (DMSO-$d_6$, 400 MHz): δ (2 isomers)=1.15-1.35 (m, 12H), 1.36-1.50 (m, 4H), 1.68-1.75 (m, 2H), 2.86 (s, 1.7H), 3.00 (s, 1.3H), 3.29-3.36 (m, 2H), 4.04 (t, 2H; J=6.4 Hz), 5.61-5.65 (m, 1H), 6.06-6.13 (m, 1H), 6.72 (dd, 1H; J=10.7 Hz, 16.9 Hz), 7.03-7.08 (m, 2H), 7.73 (d, 1H; J=8.4 Hz), 12.89 (br, 2H).

$^{13}$C-NMR (DMSO-$d_6$, 100 MHz): δ=24.3, 24.8, 25.2, 25.5, 27.3, 27.5, 27.6, 27.7, 27.8, 27.9, 32.2, 33.7, 45.8, 47.8, 66.9, 112.3, 114.2, 121.3, 125.6, 127.2, 127.6, 130.1, 136.0, 159.7, 164.0, 166.2, 168.1.

Example 2

Radical Photopolymerization of the Phthalic Acid Acrylamide AAUPA from Example 1

A mixture of 2.97 g of the phthalic acid acrylamide AAUPA, 6.95 g of the cross-linker N,N'-diethyl-1,3-bis(acrylamido)-propane, 0.03 g of the photoinitiator camphorquinone and 0.05 g of the amine accelerator 4-(dimethylamino)-benzoic acid ester was prepared. A drop of the mixture was placed on a glass plate, covered with a PET film and irradiated with a polymerization lamp (Bluephase; Ivoclar Vivadent AG, light intensity 1000 mW/cm-2) for 20 s: The irradiated sheet was then cured. The mixture was further examined by means of photo DSC (Perkin Elmer DSC 7) and a polymerization heat of 301 J/g was shown.

Example 3

Examination of the Hydrolysis Stability of the Phthalic Acid Acrylamide AAUPA from Example 1

A solution of 5% of the phthalic acid acrylamide AAUPA stabilized with 200 ppm 2,6-di-t-butyl-4-methylphenol, 5% phosphoric acid $d_3$, 10% $D_2O$ and 80% DMSO-$d_6$ was prepared, was stored at 37° C. and examined spectroscopically with $^1$H-NMR. After a standing time of 12 weeks, no changes were able to be established in the $^1$H-NMR spectrum.

Example 4

Preparation of a Light-Curing Adhesive Based on the Phthalic Acid Acrylamide AAUPA from Example 1

To examine the dentine adhesion on bovine tooth dentine, adhesives with the composition given in Table 1 were prepared.

Bovine teeth were then embedded in plastic cylinders such that the dentine and the plastic were on one plane. After 15 s etching with 37% phosphoric acid, the teeth were rinsed thoroughly with water. A layer of adhesive was then brushed on with a microbrush, briefly blown with an air blower to remove the solvent and exposed to light for 10 s with a halogen lamp (Astralis® 7, Ivoclar Vivadent AG). A composite cylinder of a dental composite material (Tetric EvoCeram, Ivoclar Vivadent AG) in two layers of 1-2 mm each was polymerized onto the adhesive layer. The testpieces were then stored in water for 24 h at 37° C. and the adhesive shear strength determined according to the ISO guideline "ISO 1994-ISO TR 11405: Dental Materials Guidance on Testing of Adhesion to Tooth Structure" and at 31.0 MPa (adhesive A) and 18.2 MPa (adhesive B) respectively.

TABLE 1

| Composition of the adhesives (values in wt.-%) | | |
|---|---|---|
| Component | Adhesive A | Adhesive B (comparison) |
| AAUPA (Ex. 1) | 10.9 | — |
| 4-MET[4] | — | 10.9 |
| Glycerol dimethacrylate | 9.9 | 9.9 |
| UDMA[1] | 9.9 | 9.9 |
| Bis-GMA[2] | 32.7 | 32.7 |
| 2-Hydroxyethyl methacrylate | 14.9 | 14.9 |
| Photoinitiator[3] | 1.7 | 1.7 |
| Ethanol (abs.) | 20.0 | 20.0 |

[1]UDMA
[2]Bis-GMA
[3]Mixture of camphorquinone (0.3%), 4-Dimethyl-benzoic acid ethyl ester (0.4%) and the acylphosphine oxide Lucerin TPO (1.0%, BASF)
[4]4-Methacryloyloxyethyl trimellitic acid The results demonstrate a very good dentine adhesion with the adhesive based on the hydrolysis-stable phthalic acid derivative AAUPA.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:
1. Dental material, comprising a polymerizable phthalic acid derivative of the general Formula I:

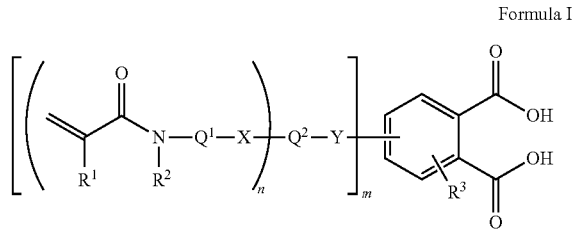

Formula I in which
$R^1$=H, methyl,
$R^2$=a $C_1$-$C_4$alkyl residue,
$Q^1$=is absent or is a $C_2$-$C_{12}$ alkylene residue, wherein the carbon chain can be interrupted by O,
$Q^2$=is absent or is a (n+1)-valent aliphatic $C_1$-$C_{10}$ residue, wherein the carbon chain can be interrupted by O and wherein $Q^1$ and $Q^2$ cannot be absent simultaneously, X=is absent, is O, S or (—CO—NR$^4$—), wherein R$^4$ is H, CH$_3$ or C$_2$H$_5$,

Y=O, n, m=independently of one another in each case mean 1 or 2,

R$^3$=is H, CH$_3$, C$_2$H$_5$ or OCH$_3$, and wherein the two carboxyl groups of the benzene ring can together form an anhydride group.

2. Dental material according to claim 1, wherein at least one of the variables has one of the following meanings:

R$^1$=H or methyl,

R$^2$=methyl or ethyl,

Q$^1$=a C$_2$-C$_{12}$ alkylene residue, wherein the chain can be interrupted by O, Q$^2$=is absent or is a (n+1)-valent aliphatic C$_1$-C$_8$ residue, wherein the chain can be interrupted by O and wherein Q$^1$ and Q$^2$ cannot be absent simultaneously, X=is absent,

Y=O, n, m=independently of one another are 1 or 2,

R$^3$=H, CH$_3$, or OCH$_3$.

3. Dental material according to claim 1, comprising one or more additional radically polymerizable monomers as co-monomers.

4. Dental material according to claim 3, comprising methyl, ethyl, hydroxyethyl, butyl, benzyl, tetrahydrofurfuryl or isobornyl (meth)acrylate, bisphenol-A-di(meth)acrylate, bis-GMA, which is an addition product of methacrylic acid and bisphenol-A-diglycidyl ether, UDMA, which is an addition product of 2-hydroxyethyl methacrylate and 2,2,4-trimethylhexamethylene diisocyanate, di-, tri- or tetraethylene glycol di(meth)acrylate, trimethylolpropane tri(meth)acrylate, pentaerythritol tetra(meth)acrylate, glycerol di(meth)acrylate, 1,4-butanediol di(meth)acrylate, 1,10-decanediol di(meth)acrylate, 1,12-dodecanediol di(meth)acrylate, and/or one or more N-mono- or disubstituted acrylamides, N-ethylacrylamide, N,N-dimethacrylamide, N-(2-hydroxyethyl)acrylamide or N-methyl-N-(2-hydroxyethyl)acrylamide, one or more N-monosubstituted methacrylamides, N-ethyl-methacrylamide, N-(2-hydroxyethyl)methacrylamide, N-vinylpyrrolidone, one or more cross-linking allyl ethers, and/or one or more cross-linking pyrrolidones, 1,6-bis(3-vinyl-2-pyrrolidonyl)-hexane, one or more cross-linking bisacrylamides, methylene or ethylene bisacrylamide, one or more cross-linking bis (meth) acrylamides, N,N'-diethyl-1,3-bis(acrylamido)-propane, 1,3 -bis(methacrylamido)-propane, 1,4-bis(acrylamido)-butane, 1,4-bis(acryloyl)-piperazine, or a mixture thereof.

5. Dental material according to claim 1, comprising one or more radically polymerizable, acid-group-containing monomers as adhesive monomers.

6. Dental material according to claim 5, comprising maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine, 4-vinylbenzoic acid, and/or vinylphosphonic acid, 4-vinylphenylphosphonic acid, 4-vinylbenzylphosphonic acid, 2methacryloyloxyethylphosphonic acid, 2-methacrylamidoethylphosphonic acid, 4-meth-acrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- or -2,4,6-trimethylphenyl ester, and/or 2-methacryloyloxypropyl mono- or dihydrogen phosphate, 2-methacryloyloxyethylphenyl hydrogen phosphate, dipentaerythritol-pentamethacryloyloxyphosphate, 10-meth-acryloyloxydecyl dihydrogen phosphate, phosphoric acid mono-(1-acryloyl-piperidine-4-yl)-ester, 6-(methacrylamido)hexyl dihydrogen phosphate, 1,3-bis-(N-acryloyl-N-propyl-amino)-propane-2-yl-dihydrogen phosphate, and/or vinylsulphonic acid, 4-vinylphenylsulphonic acid, 3-(methacrylamido)propyl sulphonic acid, or a mixture thereof.

7. Dental material according to claim 1, which comprises an initiator for radical polymerization.

8. Dental material according to claim 1, which comprises organic and/or inorganic filler.

9. Dental material according to claim 1, which comprises solvents, stabilizers, flavourings, dyes, microbiocidal active ingredients, fluoride-ion-releasing additives, optical brighteners, plasticizers and/or UV absorbers.

10. Dental material according to claim 1, which comprises a) 0.1 to 50 wt.-% polymerizable phthalic acid derivative of the general Formula I, b) 0.01 to 10 wt.-% initiator, c) 0 to 80 wt.-% co-monomer, d) 0 to 30 wt.-% adhesive monomer, e) 0 to 80 wt.-% filler, f) 0 to 70 wt.-% solvent.

11. Dental material according to claim 10 for use as an adhesive which contains 0 to 20 wt.-% filler.

12. Dental material according to claim 10 for use as a composite which contains 20 to 80 wt.-% filler.

13. Dental material according to claim 1, which comprises a) 1 to 40 wt.-% polymerizable phthalic acid derivative of the general Formula I, b) 0.1 to 3.0 wt.-% initiator, c) 0 to 60 wt.-% co-monomer, d) 0 to 15 wt.-% adhesive monomer, e) 0 to 80 wt.-% filler, f) 0 to 60 wt.-% solvent.

14. Dental material according to claim 13 for use as an adhesive which contains 0 to 20 wt.-% filler.

15. Dental material according to claim 13 for use as a composite which contains 20 to 80 wt.-% filler.

16. Dental material according to claim 1, which comprises a) 2 to 30 wt.-% polymerizable phthalic acid derivative of the general Formula I, b) 0.01 to 10 wt.-% initiator, c) 5 to 50 wt.-% co-monomer, d) 0 to 30 wt.-% adhesive monomer, e) 0 to 80 wt.-% filler, f) 0 to 50 wt.-% solvent.

17. Dental material according to claim 16 for use as an adhesive which contains 0 to 20 wt.-% filler.

18. Dental material according to claim 16 for use as a composite which contains 20 to 80 wt.-% filler.

19. A method of using a compound of Formula I for the preparation of a dental material, wherein Formula I comprises

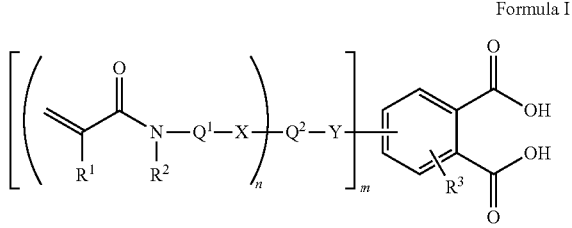

Formula I in which
R$^1$=H or methyl,
R$^2$=a C$_1$-C$_4$ alkyl residue,
Q$^1$=is absent or is a C$_2$-C$_{12}$ alkylene residue, wherein the carbon chain can be interrupted by O,
Q$^2$=is absent or is a (n+1)-valent aliphatic C$_1$-C$_{10}$ residue, wherein the carbon chain can be interrupted by O and wherein Q$^1$ and Q$^2$ cannot be absent simultaneously,
X=is absent, is O, S or (—CO—NR$^4$—), wherein R$^4$ is H, CH$_3$ or C$_2$H$_5$,
Y=O,
n, m=independently of one another in each case mean 1 or 2,
R$^3$=is H, CH$_3$, C$_2$H$_5$ or OCH$_3$, and wherein the two carboxyl groups of the benzene ring can together form an anhydride group,
the method comprising preparing the compound of Formula I and mixing it with one or more of an initiator, a co-monomer, an adhesive monomer, a filler and a solvent.

20. The method of claim 19, wherein the method comprises preparing an adhesive or a cement or a self-etching adhesive or a self-etching cement.

21. Dental material according to claim 1, wherein at least one of the variables has one of the following meanings:
R$^1$=H,
R$^2$=methyl,
Q$^1$=a linear C$_2$-C$_6$ alkylene residue;
Q$^2$=is absent or is a (n+1)-valent aliphatic C$_1$-C$_8$ residue, wherein the chain can be interrupted by O and wherein Q$^1$ and Q$^2$ cannot be absent simultaneously,
X=is absent,
Y=O,
n, m=independently of one another are 1 or 2,
R$^3$=H, CH$_3$, or OCH$_3$.

* * * * *